US008527033B1

(12) United States Patent
Williams et al.

(10) Patent No.: US 8,527,033 B1
(45) Date of Patent: Sep. 3, 2013

(54) SYSTEMS AND METHODS FOR ASSISTING WITH INTERNAL POSITIONING OF INSTRUMENTS

(75) Inventors: Keith Williams, Seattle, WA (US); Paul Thurman Dunham, Bothell, WA (US); Steven Russell Marquis, Fall City, WA (US)

(73) Assignee: SonoSite, Inc., Bothell, WA (US)

( * ) Notice: Subject to any disclaimer, the term of this patent is extended or adjusted under 35 U.S.C. 154(b) by 192 days.

(21) Appl. No.: 12/829,163

(22) Filed: Jul. 1, 2010

(51) Int. Cl.
*A61B 5/05* (2006.01)
*A61B 8/00* (2006.01)
*A61M 5/00* (2006.01)

(52) U.S. Cl.
USPC ............................ 600/424; 600/439; 604/117

(58) Field of Classification Search
USPC ................ 600/424, 437, 459, 439, 464, 443, 600/473, 476; 604/117; 382/128
See application file for complete search history.

(56) References Cited

U.S. PATENT DOCUMENTS

| | | | |
|---|---|---|---|
| 8,086,298 B2 * | 12/2011 | Whitmore et al. | 600/424 |
| 2005/0131291 A1 * | 6/2005 | Floyd et al. | 600/424 |
| 2005/0171522 A1 * | 8/2005 | Christopherson | 606/34 |
| 2007/0049822 A1 * | 3/2007 | Bunce et al. | 600/437 |
| 2007/0250006 A1 | 10/2007 | Court et al. | |
| 2009/0137907 A1 | 5/2009 | Takimoto et al. | |
| 2009/0306509 A1 * | 12/2009 | Pedersen et al. | 600/446 |

OTHER PUBLICATIONS

United States Patent and Trademark Office, Final Office Action, U.S. Appl. No. 12/752,530, mailed Jul. 23, 2012, 10 pages.

\* cited by examiner

*Primary Examiner* — Long V. Le
*Assistant Examiner* — Katherine Fernandez
(74) *Attorney, Agent, or Firm* — Perkins Coie LLP (57) ABSTRACT

Systems and methods which determine the position of an instrument internal to an object using an opto-mechanical sensor are shown. Embodiments utilize an opto-mechanical sensor system in which a mechanical instrument interface provides instrument movement information to a corresponding optical sensor system to determine instrument movement. Determinations of instrument movement preferably provide information regarding movement direction and speed. Such information, when used in combination with other information such as starting position or starting position offset, insertion angle or angle of attack, and/or insertion plane, is utilized by embodiments of the invention to determine the position of an instrument or portion thereof. Embodiments are adapted to accommodate different instrument configurations. Position information may be utilized in combination with an ultrasound image to display a visual representation of the instrument, or portion thereof, within a object being imaged.

16 Claims, 6 Drawing Sheets

SYSTEMS AND METHODS FOR ASSISTING WITH INTERNAL POSITIONING OF INSTRUMENTS

CROSS-REFERENCE TO RELATED APPLICATIONS

The present application is related to co-pending and commonly assigned U.S. patent application Ser. No. 12/752,595 entitled "Systems and Methods to Assist with Internal Positioning of Instruments," filed Apr. 1, 2010, Ser. No. 12/790,109 entitled "Systems and Methods for Enhanced Imaging of Objects Within an Image," filed May 28, 2010, and Ser. No. 12/752,530 entitled "Systems and methods for Using Imaging to Assist with Internal Positioning of Non-Modified Instruments," filed Apr. 1, 2010, the disclosures of which are hereby incorporated herein by reference.

TECHNICAL FIELD

This disclosure relates to techniques for aiding internal procedures and, more particularly, to systems and methods for using imaging to assist with internal positioning of instruments.

BACKGROUND OF THE INVENTION

Many medical procedures require precise positioning of an instrument internal to a patient. For example, interventional instruments, such as needles or catheters, are used to obtain tissue samples (e.g., biopsies), to aspirate cysts or other objects, to deliver medication or other fluids directly into an artery or vein, etc. within or internal to a patient's body. Various devices and techniques have been tried to aid a clinician in the proper placement of the instrument.

For example, one technique utilizes a wire which is temporarily disposed in the lumen of a needle as the needle was inserted into a patient. A number of electromagnetic sensors are positioned around the patient to sense the proximity of the wire. Using triangulation techniques, the orientation and position of the needle may thus be estimated. The technique, however, is quite complicated and requires complex and expensive equipment which is limited in use to needle location estimation.

It is now common practice to use real-time ultrasound imaging to aid in the proper placement of the instrument. In such procedures the ultrasound transducer can be positioned along either the longitudinal axis of the instrument, often referred to as an in-plane technique (referring to the instrument being disposed longitudinally in the image plane of the ultrasound transducer), or transverse thereto, often referred to as an out-of-plane technique (referring to the instrument being disposed transverse or orthogonal to the image plane of the ultrasound transducer). For example, an instrument guide may be used to provide relative positioning of an instrument (e.g., a needle) and an ultrasound transducer so as to facilitate in-plane or out-of-plane techniques.

Regardless of whether an out-of-plane or in-plane technique is used, it is often very difficult to identify the instrument within a real-time ultrasound image. For example, instruments such as needles and catheters are relatively small and thus difficult to capture and display in an ultrasound image. The smooth surface of many instruments, such as needles and catheters, and their angle of insertion are often such that the instruments do not appear (or do not clearly appear) in an ultrasound image. Moreover, various structure and features within the object being imaged may obscure the instrument, or portions thereof. Even where a portion of the instrument is captured and displayed in an ultrasound image it is often difficult for a clinician to readily identify the instrument within the displayed image. However, various tissue (e.g., veins and arteries) are often disposed in close proximity and thus it is important to be able to precisely identify where the instrument is located. For example, it is often critical to accurately determine where the tip of a needle is so that procedures, such as obtaining tissue samples or medicine delivery, are not performed with an unintended target.

Accordingly, clinicians may employ alternative or supplemental techniques to identify the instrument within the image. For example, the clinician can "jiggle" the instrument to cause tissue or other internal structure to move, whereby this movement can be seen in the resulting image. Inferences can be drawn from the visible movement by the clinician as to where the tip of the instrument is presently located.

A variation on the foregoing technique is to utilize a device to induce vibration to the instrument. For example, a vibratory device may be applied to the external portion of a needle during a procedure and a Doppler image mode utilized by the ultrasound imaging system to provide artifacts in a resulting ultrasound image. However, the vibratory device is somewhat cumbersome and difficult to utilize in combination with needle insertion. Moreover, the technique results in somewhat imprecise depiction of the needle position because the color Doppler image modes used to display the needle vibration artifacts are generally of relatively low resolution which, particularly when combined with the vibration of the needle.

Other techniques have also been utilized in various attempts to provide information regarding the position of an instrument. For example, gradations or other markings may be added to the instrument itself for reference when determining its position. A needle may be provided with gradations along its shaft (e.g., 1 cm graduated markings), such that the number of gradations passing into a patient may be counted for a determination of the depth of insertion of the needle into the patient. Unfortunately, the lighting and other ambient conditions present during a procedure may not be conducive to an accurate count of such gradations. Moreover, a clinician performing a procedure is often unable to view the needle for sufficient periods of time to accurately count the passing of all gradations. For example, the clinician's view may be diverted periodically to the patient, to view other equipment, etc.

Still other techniques modify the instrument to provide facets or other perturbations upon a surface of the instrument in order to increase echogenicity of the instrument. For example, to facilitate reflection of an ultrasound signal the surface of a needle may be provided with a number of facets. An ultrasound system may thus provide an image of the needle, even with the needle is inserted at relatively acute angles, due to the facets causing ultrasound signals to be reflected toward the ultrasound transducer. Such facets have not, however, been found particularly effective in identifying particular portions of the needle, such as the tip. Moreover, the presence of the facets upon the surface of the needle affects the use of the needle, such as by causing insertion resistance, patient discomfort, etc.

A technique for determining the present position of the tip of the instrument is to insert dye or other contrast agent and observe visible changes within the resulting image. However, such a technique is often undesirable due to risks associated with injecting such media into a patient and the complexity added to the procedure associated with the use and delivery of such contras agents. Another technique for determining where the tip of the instrument is located is to modify the instrument itself (e.g., attach sensors thereto, provide visible markings thereon, and/or the like). Such techniques, however, are often undesirable due to the expense and complexity added to the procedure associated with the use of such special purpose instruments.

Another technique for determining the present position of the tip of the instrument utilizes a very small transducer disposed upon the end of a wire. The wire is inserted into the lumen of a needle so as to place the transducer at the tip. The transducer is activated during insertion of the needle to radiate ultrasound signals. A transducer of an ultrasound system receives the signals radiated by the transducer and image processing by the ultrasound system interprets these signals as a highly reflective point in the imaged volume. Thus the position of the tip may appear in the generated ultrasound image. However, the very small transducer and its associated control circuitry is relatively expensive and of use only for such procedures. Moreover, the procedure must be altered to include insertion and removal of the small transducer assembly within the needle.

From the above, it can be appreciated that when using the techniques discussed above the clinician must often guess where the tip of the instrument is and, based on this "best guess" estimation, perform the desired procedure. Alternatively, the instrument and/or the procedure may be adapted to facilitate more accurate determinations of instrument position. However, these adaptations introduce undesired complexity, risk, and cost to the procedure.

BRIEF SUMMARY OF THE INVENTION

The present invention is directed to systems and methods which determine the position of an instrument (e.g., a needle, catheter, stent, endoscope, angioplasty balloon, etc.) within an object (e.g., within the body of a patient) using an opto-mechanical sensor. Opto-mechanical sensors of embodiments are operable to provide information regarding the position of a portion of instruments, where the instruments are not specifically adapted or modified for use with a sensor herein (i.e., non-modified instrument configurations). Embodiments utilize an opto-mechanical sensor system in which a mechanical instrument interface and optical sensor system cooperate to determine instrument movement. Such determinations of instrument movement preferably provide information regarding movement direction and displacement. The foregoing movement information is utilized by embodiments of the invention to determine the position of a portion of the instrument (e.g., instrument tip). For example, movement information may be used in combination with other information (e.g., starting position, starting position offset, insertion angle, and/or insertion plane) for determining the position of a portion of the instrument.

A mechanical instrument interface of an opto-mechanical sensor system of embodiments is adapted to engage a surface of an instrument and to provide mechanical motion corresponding to movement of the instrument. Accordingly, mechanical instrument interfaces of embodiments of an opto-mechanical sensor system include an interface surface for interfacing with a surface of an instrument and a sensor surface for facilitating operation of a corresponding optical sensor system of the opto-mechanical sensor system.

An interface surface of a mechanical instrument interface operates to transfer motion of an instrument to the opto-mechanical sensor system. Accordingly, an interface surface of the mechanical instrument interface of embodiments is adapted to provide non-slip engagement of a surface of an instrument. For example, an interface surface may use a non-slip interface surface treatment, selection of an appropriate resilience of an interface surface material, etc. to provide non-slip engagement of a surface of an instrument.

A sensor surface of a mechanical instrument interface of embodiments of the mechanical instrument interface is provided motion corresponding to movement of the interface surface. Embodiments of such a sensor surface are adapted to facilitate an optical sensor system detecting the movement of the sensor surface. For example, a sensor surface may use sensor surface crenellation, sensor surface windows, sensor surface texturing, sensor surface gradations, etc. to facilitate an optical sensor system detecting the movement of the sensor surface.

Embodiments of the mechanical instrument interface are adapted to accommodate different instrument configurations (e.g., different needle gauges). For example, a mechanical instrument interface may use a movable or adjustable mechanical instrument interface mount to accommodate different needle gauges. Additionally or alternatively, embodiments of the mechanical instrument interface provide a motion multiplier, such as to facilitate improved movement detection by a corresponding optical sensor system, to facilitate high resolution movement detection, etc. For example, the mechanical instrument interface may be adapted such that the sensor surface moves at a higher velocity than does the corresponding interface surface to thereby provide a motion multiplier.

The mechanical instrument interface of opto-mechanical sensors of embodiments is adapted to provide a relatively inexpensive, simple configuration. For example, a mechanical instrument interface may be comprised of few pieces, such as small molded plastic pieces, metal pieces, etc. Such embodiments facilitate disposal of the mechanical instrument interface after use. Thus, although the mechanical instrument interface may be used within the sterile field of a particular procedure, sterility may be maintained through sterilization of the unit at manufacture and its disposal after use. A mechanical instrument interface utilized according to embodiments of the invention may additionally or alternatively be adapted to facilitate its sterilization and reuse.

An optical sensor system of an opto-mechanical sensor system of embodiments comprises a light source (e.g., a source of energy in the visible or invisible spectrum) in combination with an optical sensor to detect movement of a surface in proximity to the optical sensor (e.g., a sensor surface of a mechanical instrument interface). A light source utilized according to embodiments may comprising a light emitting diode (LED), laser diode, etc. The optical sensor system may utilize an optical encoder configuration in combination with the foregoing light source and optical sensor to detect movement. Additionally or alternatively, the optical sensor system may utilize the foregoing light source and optical sensor to take successive images of the sensor surface of the mechanical instrument interface. Likewise, the optical sensor system of embodiments may operate to collect information regarding changes in interference patterns appearing on the sensor surface for light emitted by the light source. Processing circuitry of embodiments of the optical sensor system analyzes such information to determine instrument movement.

Commercially available, off-the-shelf optical sensor components are preferably utilized in providing an optical sensor system of embodiments of the present invention. For example, commercially available sensor packages comprising an image acquisition system (IAS), associated digital signal processor (DSP), and other components are utilized in implementing an optical sensory system for use in instrument movement determination according to embodiments of the invention. Accordingly, low cost, highly miniaturized optical sensor systems may readily be provided to facilitate their unobtrusive disposition on various equipment (e.g., instrument guides, ultrasound transducer assemblies, etc.), disposability (e.g., for use in sterile environments), etc.

An opto-mechanical sensor of embodiments of the invention is preferably disposed in a known or fixed relationship to the instrument and/or other structure utilized in performing a desired procedure using the instrument. For example, an interventional instrument guide, such as a needle guide, may be utilized in cooperation with an ultrasonic transducer. The interventional instrument guide may thus provide guidance of the instrument for real-time ultrasound imaging for the procedure. An opto-mechanical sensor, including a mechanical instrument interface and optical sensor system, may be affixed to the interventional instrument guide in a known position. The opto-mechanical sensor may operate as described above to detect movement of the instrument through the guide. Information regarding the known position of the opto-mechanical sensor (e.g., on the interventional instrument guide and/or the ultrasound transducer) may be utilized by processing circuitry of the opto-mechanical sensor system of embodiments to determine a position of the instrument, or portion thereof (e.g., the tip), relative to the ultrasound transducer.

Embodiments of the invention utilize available information regarding the orientation, position, and/or movement of an instrument relative to an imaging transducer to determine where a portion of the instrument of interest (e.g., the tip) is in relation to a target. For example, by knowing the angle of insertion of the instrument (also referred to as the angle of attack), the relative position of an instrument guide, and information regarding the movement of the instrument through the instrument guide, embodiments of the invention operate to calculate the position of any desired portion of the instrument at any time.

The foregoing position information may be utilized in combination with an ultrasound image generated by an ultrasound system unit to display a visual representation of the instrument, or portion thereof, within a object being imaged (e.g., portion of a patient's internal physiology). For example, the calculated position of a portion of the instrument within the object may be superimposed onto an image generated using the imaging transducer, thereby allowing a clinician or other user to visualize the placement of the instrument.

It should be appreciated that embodiments of the foregoing opto-mechanical sensor system may be utilized to provide movement determinations for non-modified instruments. That is, movement information may be determined for an instrument (such as a needle, catheter, stent, endoscope, angioplasty balloon, etc.) that has not been specially adapted for use with an opto-mechanical sensor system of the present invention (e.g., the instrument is provided in a non-modified state for general use in performing a desired procedure). Accordingly, non-modified instruments as may be utilized according to embodiments of the invention do not include special markings, structure, sensors, appliqués, etc. for operation of opto-mechanical sensor systems herein.

Opto-mechanical sensor systems of embodiments of the invention may be utilized in combination with other instrument position detection or determination systems, if desired. For example, an opto-mechanical sensor system of an embodiment may be utilized in combination with an enhanced instrument imaging technique (e.g., an imaging technique operable to more consistently obtain images of portions of an instrument) in order to provide higher levels of confidence for instrument location determination, to provide present location determination correction, etc.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

Figure 1A:
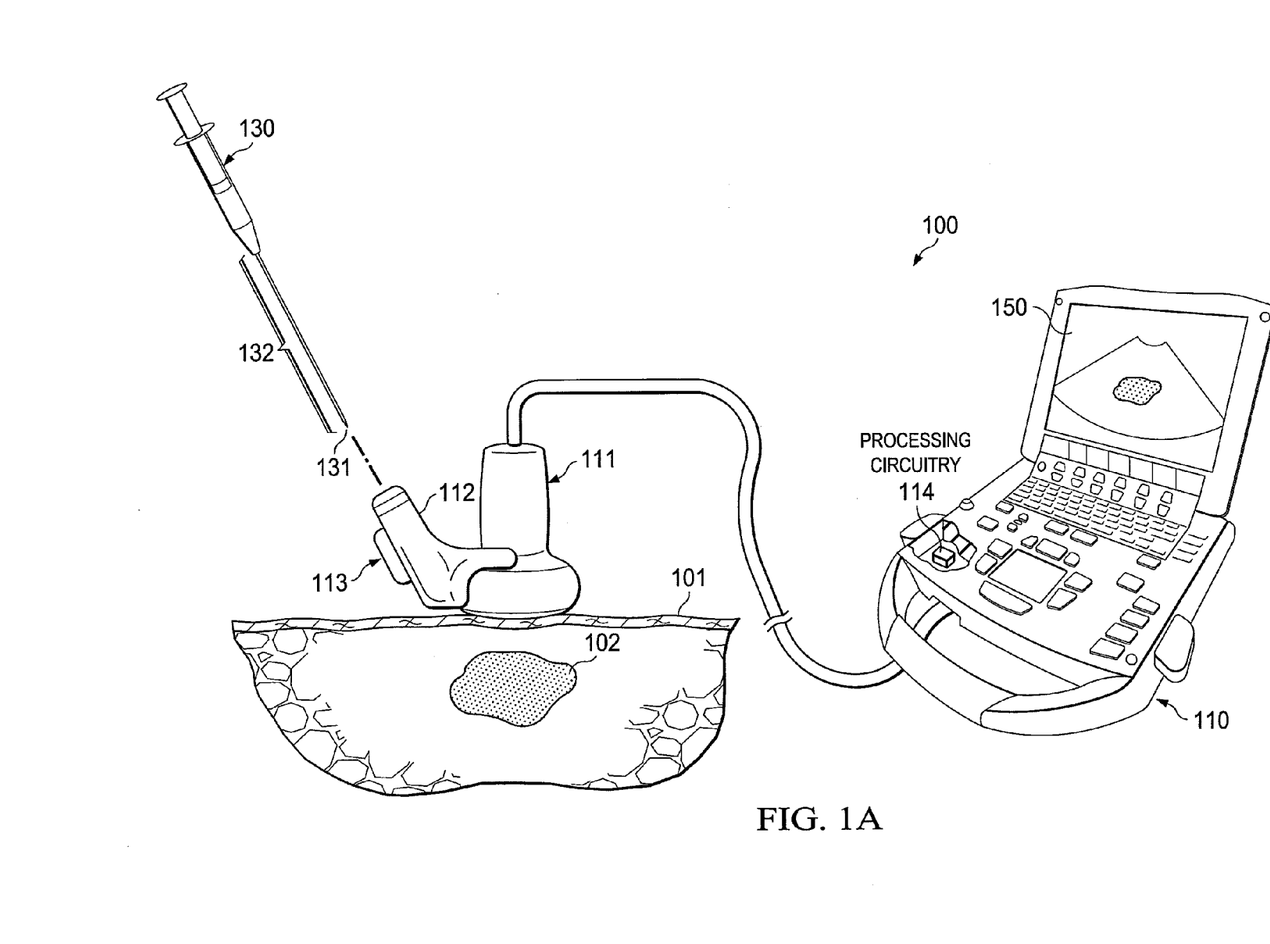
FIG. 1A shows an imaging system adapted according to an embodiment of the invention.

FIG. 1A shows an imaging system adapted according to an embodiment of the invention to determine the position of an instrument (such as a needle, catheter, stent, endoscope, angioplasty balloon, etc.), or a portion of an instrument (e.g., a needle tip) within an object using an opto-mechanical sensor system configuration. Specifically, imaging system 100 of FIG. 1A, such as may comprises an ultrasound imaging system, is adapted for use in providing real-time images for facilitating positioning a portion of instrument 130 within object 101. For example, instrument 130 may comprise a needle or other interventional instrument for insertion into object 101, such as may comprise a human body, for interfacing with one or more objects therein, such as target 102 (e.g., a cyst, tumor, blood vessel, nerve, etc.), during an interventional procedure (e.g., biopsy, injection, line insertion, etc.).

The term real-time as used herein, such as for real-time images, is intended to encompass operation, interaction, reaction, etc. which occurs sufficiently rapidly to be perceived by an operator or user as occurring in the moment. Accordingly, generation and display of real-time images may include various processing delays, signal propagation delays, etc.

Imaging system 100 may be utilized to generate an image to facilitate positioning a portion of instrument 130 within object 101, such as to dispose tip 131 at or in a desired target (e.g., target 102). Imaging transducer 111, such as may comprise an ultrasound transducer or other imaging transducer configuration, obtains imaging information from an imaging area or volume within object 101. In operation, imaging transducer 111, operable in combination with system unit 110 (e.g., an ultrasound system unit or other appropriate system unit), is used to provide image 150 showing features of the object beneath a surface of object 101 which would otherwise be invisible to the naked eye. For example, system unit 110 of the illustrated embodiment comprises processing circuitry 114 operable to provide image processing, instrument position determination, etc. Processing circuitry 114 may comprise processing logic (e.g., a general purpose central processing unit (CPU) operable under control of an instruction set, application specific integrated circuit (ASIC), programmable gate array (PGA), DSP, and/or the like) and memory (e.g., random access memory (RAM), flash memory, magnetic memory, optical memory, and/or the like). Detail regarding imaging systems which may be adapted according to the concepts of the present invention is provided in co-pending and commonly assigned U.S. patent application Ser. No. 12/467,899 entitled "Modular Apparatus for Diagnostic Ultrasound," the disclosure of which is hereby incorporated herein by reference.

Imaging transducer 111 of the illustrated embodiment is shown fitted with instrument guide 112 (e.g., a needle guide) operable to provide at least some control of movement of instrument 130. Thus, the use of instrument guide 112 provides information regarding the orientation of the instrument relative to imaging transducer 111. An instrument guide such as shown in co-pending and commonly assigned U.S. patent application Ser. No. 12/499,908 entitled "Device for Assisting the Positioning of Medical Devices" and Ser. No. 11/216,735 entitled "Medical Device Guide Locator," the disclosures of which are hereby incorporated herein by reference, may be used as instrument guide 112 to provide relative positioning of instrument 130 and imaging transducer 111 according to embodiments of the invention.

Figure 1B:
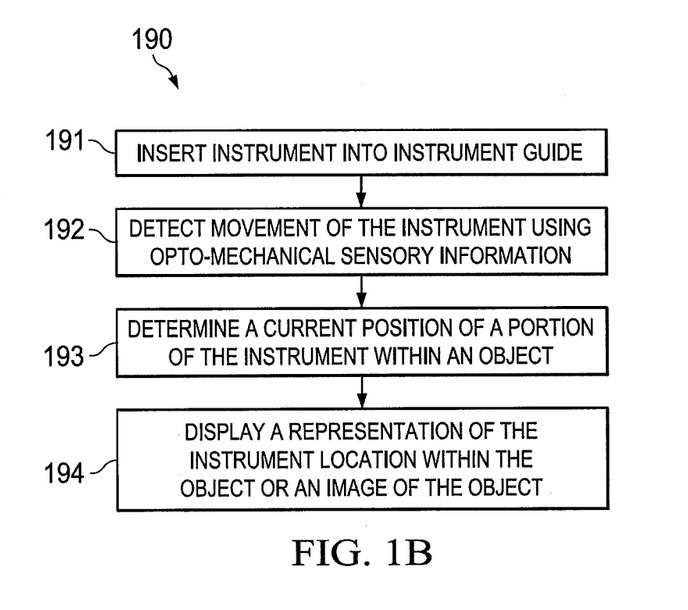
FIG. 1B shows a high level flow diagram of operation of the imaging system of FIG. 1A to provide assistance for internal positioning of an instrument according to embodiments of the invention.

FIG. 1B shows a flow diagram in which flow 190 defines operation of imaging system 100 of FIG. 1A according to embodiments of the invention. Operation in accordance with flow 90 of the illustrated embodiment provides assistance for positioning of instrument 130.

In performing a desired procedure according to embodiments of the invention, a portion of instrument 130 (e.g., shaft portion 132) is inserted into object 101 through instrument guide 112. Accordingly, shaft portion 132 of instrument 130 is inserted in instrument guide 112 at block 191 of the illustrated embodiment of flow 190.

Instrument guide 112 of embodiments restricts movement of instrument 130 in two dimensions, while allowing movement in a third dimension (e.g., direction of insertion of instrument 130). Thus, instrument guide 112 facilitates insertion of shaft portion 132 of instrument 130 into object 101 at a desired or known insertion angle (angle of attack) relative to imaging transducer 111. Through selection of an appropriate insertion angle, shaft portion 132 of instrument 130 may be appropriately guided such that tip 131 of instrument 130 is directed to interface with a target within object 101, such as target 102. Selection of an appropriate insertion angle may, for example, be accomplished by selecting an appropriately configured instrument guide or by appropriately adjusting an adjustable instrument guide.

Due to the relatively small size of the shaft portion 132 of instrument 130 which is inserted into object 101 and various other factors (e.g., obscuring structure present in object 101, the relatively narrow image plane provided by imaging transducer 111, the angle of incidence of imaging signals upon instrument 130, etc.), shaft portion 132 of instrument 130 may not be visible or clearly visible in image 150 generated by imaging system 100. Accordingly, imaging system 100 of the illustrated embodiment utilizes opto-mechanical sensor system 113 to facilitate determining the position of a portion of instrument 130 inserted into internal to object 101 (e.g., shaft portion 132 and/or tip 131).

Opto-mechanical sensor system 113 of the illustrated embodiment is integrated into or otherwise disposed upon instrument guide 112. Accordingly, opto-mechanical sensor system 113 is disposed to allow a mechanical instrument interface of opto-mechanical sensor system 113 to interface with a surface of a portion of instrument 130. This configuration facilitates instrument movement detection by an optical sensor system of opto-mechanical sensor system 113 (block 192 of FIG. 1B). For example, instrument guide 112 may comprise a lumen through which shaft portion 132 of instrument 130 is passed as shaft portion 132 of instrument 130 is inserted into object 101. A mechanical instrument interface of opto-mechanical sensor system 113 is preferably disposed so as to engage shaft portion 132 passing within instrument guide 112. As shaft portion 132 of instrument 130 moves further through instrument guide 112 (having already engaged the mechanical instrument interface), an optical sensor system of opto-mechanical sensor system 113 detects movement of the mechanical instrument interface corresponding to the movement of shaft portion 132 of instrument 132.

It should be appreciated that opto-mechanical sensor, system 113, or portions thereof, may be disposed in different configurations than that shown in the embodiment of FIG. 1A. For example, opto-mechanical sensor system 113 may be disposed upon imaging transducer 111 rather than instrument guide 112. Opto-mechanical sensor system 113 may additionally or alternatively be disposed in a distributed configuration, such as to dispose an opto-mechanical sensor thereof upon instrument guide 112 or imaging transducer 111 and processing circuitry thereof within system unit 110. Irrespective of the particular configuration of opto-mechanical sensor system 113, as will be better understood from the discussion which follows, a relative position of the aforementioned opto-mechanical sensor relative to imaging transducer 111 is preferably known, input by a user, or otherwise determinable.

Figure 2A:
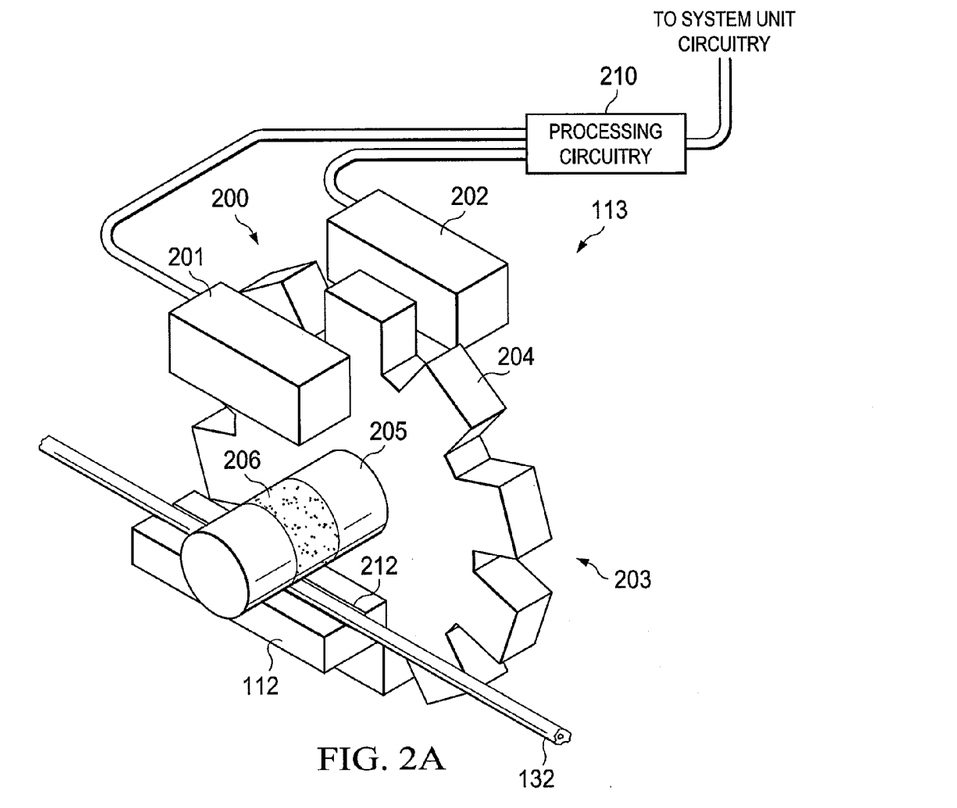
FIGS. 2A-2C show detail of an embodiment of an opto-mechanical sensor system of the imaging system of FIG. 1A.
Figure 2B:
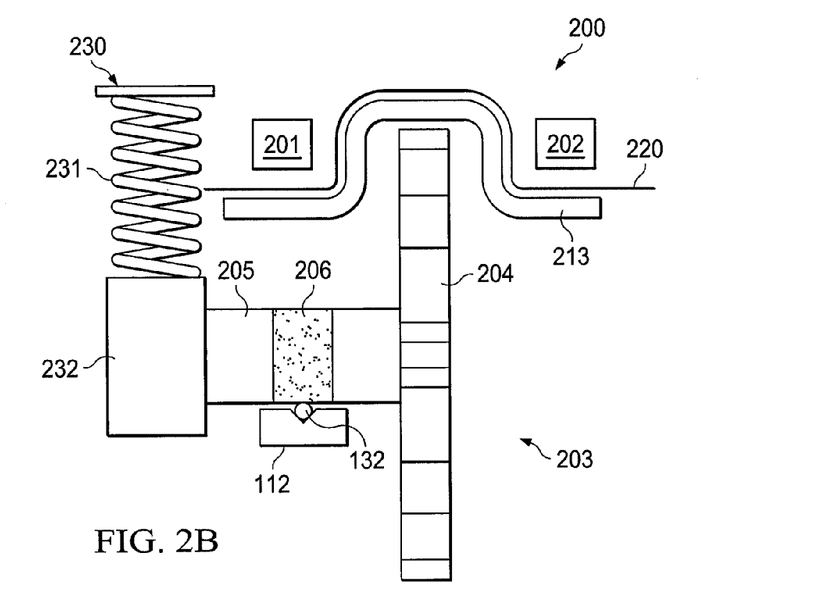
Figure 2C:
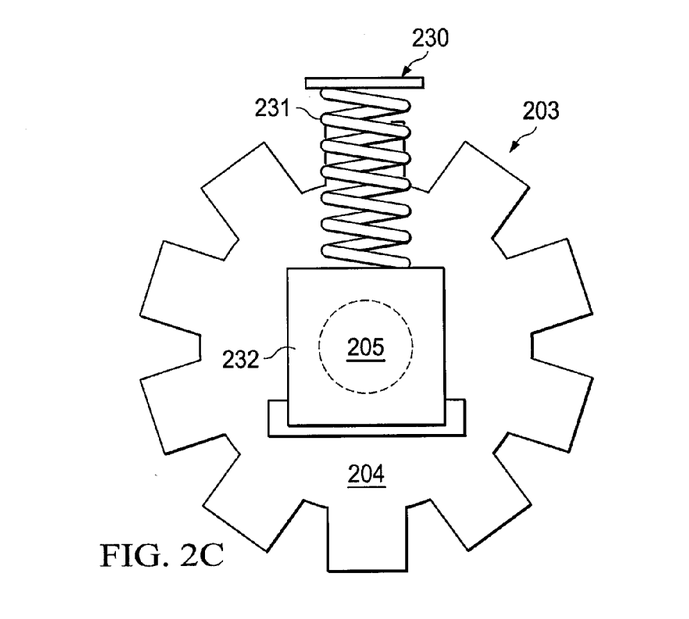

FIGS. 2A-2C show detail of an embodiment of opto-mechanical sensor system 113. The embodiment of opto-mechanical sensor system 113 shown in FIGS. 2A-2C comprises optical sensor system 200 and mechanical instrument interface 203. Opto-mechanical sensor system 113 of the illustrated embodiment further comprises processing circuitry 210 in communication with light source 201 and optical sensor 202 as well as with circuitry of system unit 110 (FIG. 1A).

Optical sensor system 200 of the embodiment of opto-mechanical sensor system 113 illustrated in FIGS. 2A-2C includes light source 201 and optical sensor 202. Light source 201 of embodiments may comprise a LED, laser diode, or other light source to provide appropriate illumination for corresponding operation of optical sensor 202. Optical sensor 202 may comprise one or more charge-coupled device (CCD), phototransistor, photodiode, and/or other sensor device.

Mechanical instrument interface 203 of the embodiment of opto-mechanical sensor system 113 shown in FIGS. 2A-2C includes sensor surface 204 and interface surface 205. Sensor surface 204 and interface surface 205 are coupled such that as interface surface 205 is rotated, sensor surface 204 also rotates. Sensor surface 204 of the illustrated embodiment is crenellated and thus includes a plurality of merlons disposed along its circumference operable to interrupt the transmission of light between light source 201 and optical sensor 202 as sensor surface 204 is rotated. The number, size, and spacing of the merlons is selected to provide desired movement detection resolution by operation of optical sensor system 200. Embodiments may implement different optical encoder techniques, such as by using slits or windows disposed in sensor surface 204 in addition to or in the alternative to crenels and merlons of the illustrated embodiment.

In operation, energy emitted by light source 201 and directed toward sensor devices of optical sensor 202 is interrupted by the merlons of sensor surface 204 as mechanical instrument interface 203 is rotated. The speed at which light pulses are detected by optical sensor 202 provides information regarding the speed at which mechanical instrument interface 203 is rotating. The timing of light pulses being received by different sensor devices of optical sensor 202 provides information regarding the direction mechanical instrument interface 203 is rotating.

Instrument support portion 212 of instrument guide 112 preferably holds shaft portion 132 of instrument 130 as shaft portion 132 of instrument 130 is inserted into object 101. Thus movement inserting shaft portion 132 into or extracting shaft portion 132 from instrument guide 112 causes a surface of shaft portion 132 of instrument 130 to engage interface surface 205 of mechanical instrument interface 203. As instrument 130 is moved interface surface 205 is rotated by movement of instrument 130 which in turn rotates sensor surface 204. Optical sensor 202 captures light pulses corresponding to the speed and direction of movement of instrument 130 for use in determining its movement.

A surface of instrument 130, such as the surface of shaft portion 132, may provide a relatively smooth, substantially featureless topology, particularly in embodiments where instrument 130 has not been specially adapted or otherwise modified for movement or position determinations. Embodiments of interface surface 205 are thus adapted to provide non-slip engagement of a surface of an instrument. For example, embodiments of interface surface 205 use a non-slip interface surface treatment, selection of an appropriate resilience of an interface surface material, etc. Non-slip surface 206 (FIG. 2B), for example, may be provided to ensure accurate and reliable communication of movement between shaft portion 132 of instrument 130 and interface surface 205. Non-slip surface 206 may comprise a rubber, foam, or other surface providing suitable surface friction.

In operation according to embodiments, optical sensor 202 provides one or more series of pulses to processing circuitry 210 for processing to determine motion of instrument 130 (block 192 of FIG. 1B). Processing circuitry 210 of embodiments comprises processing logic (e.g., a general purpose CPU operable under control of an instruction set, ASIC, PGA, DSP, and/or the like) and memory (e.g., RAM, flash memory, magnetic memory, optical memory, and/or the like) operable to receive information provided by optical sensor 202 and determine movement information therefrom. For example, embodiments of processing circuitry 210 operates to analyze pulses provided by a plurality of sensor devices of optical sensor 202 to determine movement direction, velocity, and/or the like shaft portion 132 of instrument 130 through instrument guide 112. Processing circuitry 210 may thus provide movement information (e.g., movement along the axis of the insertion angle) to processing circuitry 114 of system unit 110 (FIG. 1A). This movement information may be utilized in instrument position determination, image generation, etc.

Communication of information between processing circuitry 210 and processing circuitry 114 may be by wireline (e.g., within or as part of a signal cable connecting imaging transducer 111 and system unit 110) or wireless (e.g., RF or infrared (IR)). Similarly, communication of information between processing circuitry 210 and light source 201 and/or optical sensor 202 may be by wireline or wireless. For example, where opto-mechanical sensor system 113 is provided in a distributed configuration, such as where processing circuitry 210 is disposed within a housing of system unit 110, wireless communication of information controlling light source 201 and information captured by optical sensor 202 may be provided using BLUETOOTH, WIFI (IEEE 802.11), or other wireless protocols (including standardized and proprietary protocols). Alternatively, wireline communication for such information may be provided using universal serial bus (USB), inter-integrated circuit ($I^2C$) bus, or other wireline protocols (including standardized and proprietary protocols). Where opto-mechanical sensor system 113 is provided in a compact configuration, such as where processing circuitry 210 is disposed in close proximity to light source 201 and optical sensor 202, wireless communication of derived movement information may be provided using BLUETOOTH, WIFI (IEEE 802.11), or other wireless protocols (including standardized and proprietary protocols). Alternatively, wireline communication for such information may be provided using USB, $I^2C$ bus, or other wireline protocols (including standardized and proprietary protocols).

It should be appreciated that, although shown separately in the illustrated embodiment, processing circuitry 210 and 114, or portions thereof, may be combined according to embodiments to provide operation as described herein. For example, processing circuitry 210 may perform one or more of the functions discussed with reference to processing circuitry 114 and/or processing circuitry 114 may perform one or more of the functions discussed with reference to processing circuitry 210.

To accommodate different instrument sizes (e.g., different needle gages), embodiments of mechanical instrument interface 203 comprise a movable or adjustable mount. The illustrated embodiment of mechanical instrument interface 203 comprises movable mount 230 including bias 231 and movable receiver 232. Movable receiver 232 provides support for mechanical instrument interface 203 by a portion of interface surface 205 being disposed in movable receiver 232. Bias 231 encourages movable receiver 232 towards instrument support portion 212 of instrument guide 112. Instrument support portion 212 of instrument guide 112 may correspondingly be adapted to accommodate different sizes of instruments. For example, instrument support portion 212 may comprise a "V" groove or other instrument guide. The movable receiver and bias configuration of movable mount 230 allows mechanical instrument interface 203 to move relative to instrument support portion 212 of instrument guide 112 to accommodate instruments of different or differing (e.g., tapered shaft) sizes.

It should be appreciated that mechanical instrument interface 203 of the illustrated embodiment provides a relatively inexpensive, simple configuration. Such an embodiment facilitates a sterile procedure implementation wherein mechanical instrument interface 203 is discarded after use. Although mechanical instrument interface 203 may be discarded, optical sensor system 200 of embodiments may be reused. Thus, although mechanical instrument interface 203 may be disposed within the sterile field of a particular procedure, sterility may be maintained through sterilization of the unit at manufacture and its disposal after its use.

To facilitate the reuse of optical sensor system 200, embodiments of the invention provide sterile field separation between mechanical instrument interface 203 and optical sensor system 200. For example, resilient membrane portion 220 (FIG. 2B) of a sterile drape may be disposed between a mechanically separable (e.g., snap together) configuration of mechanical instrument interface 203 and optical sensor system 200. To provide suitable distortion of the sterile drape to accommodate sensor surface 204, sensor energy transparent window 213 is provided in the illustrated embodiment. Sensor energy transparent window 213 of the illustrated embodiment provides a rigid shape for preventing a portion of a sterile drape disposed between optical sensor system 200 and mechanical instrument interface 203 from interfering with the movement of mechanical instrument interface 203. To accommodate the aforementioned transmission of light between light source 201 and optical sensor 202 of optical sensor system 200, sensor energy transparent window 213 and the aforementioned portion of the sterile drape are adapted to pass light energy emitted by light source 201.

It should be appreciated that sensor energy transparent window 213 may be utilized without the aforementioned sterile drape, if desired. For example, sensor energy transparent window 213 may be utilized to isolate optical sensor system 200 from fluids and other media which may be present in, introduced into, or infiltrate the lumen of instrument guide 112.

Embodiments of opto-mechanical sensor system 113 may omit sensor energy transparent window 213 and/or resilient membrane portion 220 of a sterile drape if desired. For example, where opto-mechanical sensor system 113 is disposable or where optical sensor system 200 is adapted to facilitate its sterilization and reuse, sensor energy transparent window 213 and/or resilient membrane portion 220 may be omitted. Similarly, mechanical instrument interface 203 utilized according to embodiments of the invention may additionally or alternatively be adapted to facilitate its sterilization and reuse.

Figure 3:
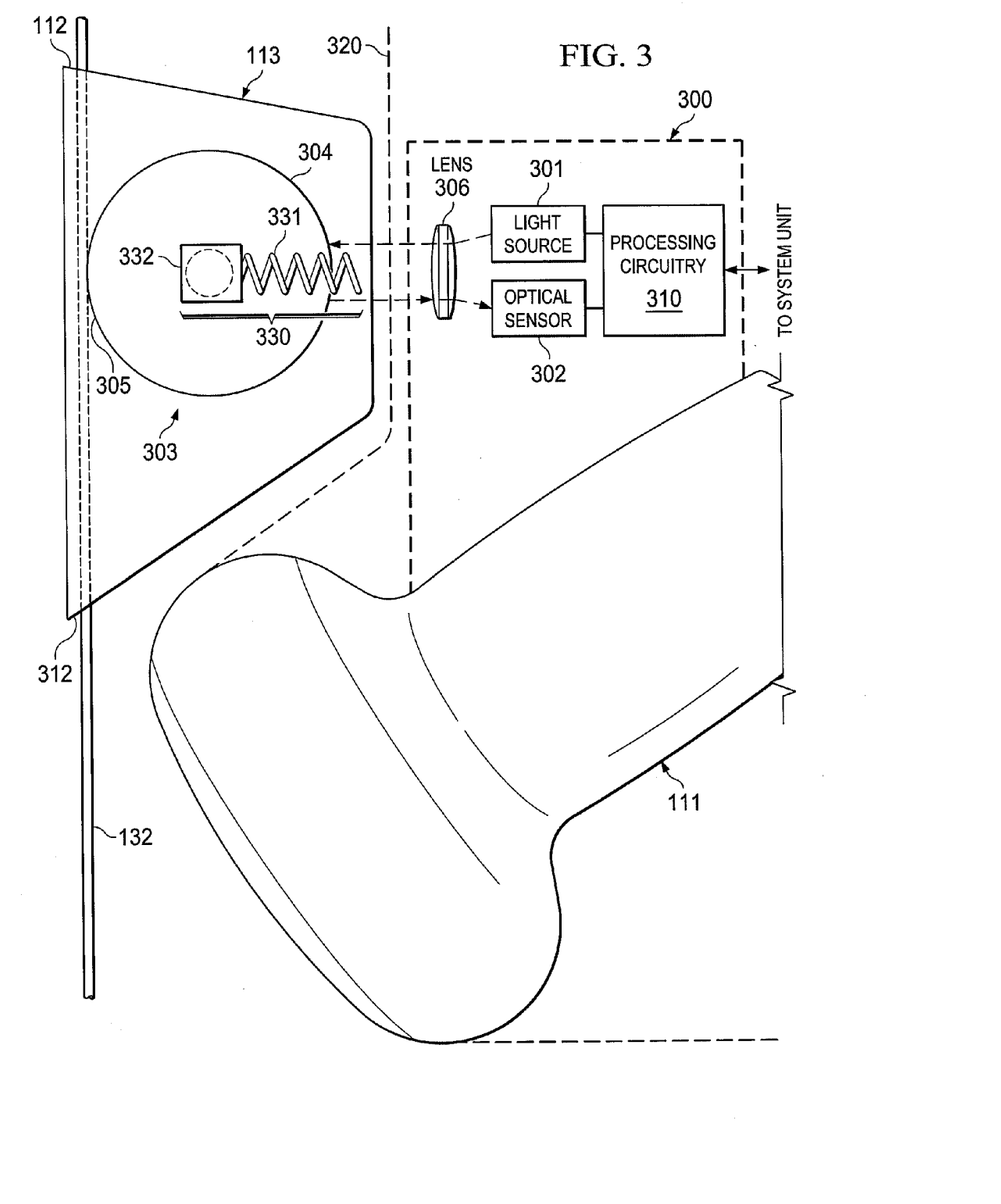
FIG. 3 shows detail of another embodiment of an opto-mechanical sensor system of the imaging system of FIG. 1A.

FIG. 3 shows detail of another embodiment of opto-mechanical sensor system 113. The embodiment of FIG. 3 comprises optical sensor system 300 and mechanical instrument interface 303. The illustrated embodiment of opto-mechanical sensor system 113 further comprises processing circuitry 310 in communication with optical sensor system 300 as well as with circuitry of system unit 110 (FIG. 1A).

Optical sensor system 300 of the illustrated embodiment includes light source 301, optical sensor 302, and lens 306. Light source 301 of embodiments may comprise a LED, laser diode, or other light source to provide appropriate illumination for corresponding operation of optical sensor 302. Optical sensor 302 may comprise one or more charge-coupled device (CCD), phototransistor, photodiode, and/or other sensor device.

Mechanical instrument interface 303 of the embodiment of FIG. 3 includes a wheel configuration providing both sensor surface 304 and interface surface 305 (sensor surface 304 and interface surface 305 being co-located in this embodiment). Mechanical instrument interface 303 of the illustrated embodiment is configured such that the circumferential surface thereof (providing interface surface 305) is disposed to interface with shaft portion 132 of instrument 130 is passed through instrument guide 112. Moreover, mechanical instrument interface 303 of the illustrated embodiment is configured such that the circumferential surface thereof (also providing sensor surface 304) is disposed to be "viewed" by optical sensor system 300.

In operation, energy emitted by light source 301 and reflected off of sensor surface 304 is focused upon sensor devices of optical sensor 302 by lens 306. Optical sensor 302 may thus capture "images" of sensor surface 304 for use in determining movement. It should be appreciated that the foregoing images may capture information other than that which is perceived as an image by a human. For example, embodiments collect information regarding changes in interference patterns appearing on sensor surface 304 from light emitted by the light source (e.g., where light source 301 comprises a laser light source).

Instrument support portion 312 of instrument guide 112 preferably holds shaft portion 132 of instrument 130 as shaft portion 132 is inserted into object 101. Thus movement inserting shaft portion 132 into or extracting shaft portion 132 from instrument guide 112 causes a surface of shaft portion 132 of instrument 130 to engage interface surface 305 of mechanical instrument interface 303. As instrument 130 is moved interface surface 305, and thus sensor surface 304, is rotated. The embodiment of optical sensor system 113 illustrated in FIG. 3 is disposed in juxtaposition with mechanical instrument interface 303, or a portion thereof, to provide a view of at least a portion of sensor surface 304. Thus, light source 301 and optical sensor 302 may cooperate to illuminate and capture images of sensor surface 304 and obtain information regarding its movement.

A surface of instrument 130 may provide a relatively smooth, substantially featureless topology, particularly in embodiments where instrument 130 has not been specially adapted or otherwise modified for movement or position determinations. Embodiments of interface surface 305 of mechanical instrument interface 303 are thus adapted to provide non-slip engagement of a surface of an instrument. For example, embodiments of interface surface 305 may use a non-slip interface surface treatment, selection of an appropriate resilience of an interface surface material, etc. According to an embodiment, a non-slip surface (not shown) (e.g., a rubber, foam, or other surface providing suitable surface friction) may be provided to ensure accurate and reliable communication of movement between shaft portion 132 of instrument 130 and interface surface 305.

Additionally or alternatively, sensor surface 304 of mechanical instrument interface 303 may be adapted to facilitate movement detection by operation of optical sensor system 300. For example, gradations, texture, grooves, surface perturbations, and/or other features may be provided upon sensor surface 304 to ensure accurate and reliable detection of movement by optical sensor system 300. The number, size, spacing, shape, type, etc. of such features are preferably selected to provide desired movement detection resolution by operation of optical sensor system 300.

Embodiments of a mechanical instrument interface of opto-mechanical sensor system 113 may be adapted to facilitate movement detection by a corresponding optical sensor system through a motion multiplier configuration. For example, using a concentric axel arrangement (e.g., similar to the relationship of interface surface 205 to sensor surface 204 of FIGS. 2A-2C), an interface surface having a smaller circumference may be in communication with a sensor surface having a larger circumference. Such a concentric axel arrangement provides multiplication of the rotational motion by the ratio of the size of the circumferences. Similarly, a geared configuration may be implemented to provide such motion multiplication. Irrespective of the particular technique by which it is provided, such motion multiplication may be utilized to provide finer movement detection resolution, avoid errors in movement detection, etc.

Although instrument 130 may present a relatively small surface area (e.g., narrow profile) for movement detection, embodiments of a sensor surface utilized herein are adapted to present a larger sensor surface to optical sensor system 300. For example, the width of sensor surface 304 (FIG. 3) may be appreciably wider (e.g., 2-3 times wider) than a width of shaft portion 132 of instrument 130 passing through instrument guide 112.

In operation according to embodiments, optical sensor 302 provide a series of captured "images" of the sensor surface to processing circuitry 310 for processing to determine motion of instrument 130 (block 192 of FIG. 1B). Processing circuitry 310 of embodiments comprises processing logic (e.g., a general purpose CPU operable under control of an instruction set, ASIC, PGA, DSP, and/or the like) and memory (e.g., RAM, flash memory, magnetic memory, optical memory, and/or the like) operable to receive information provided by optical sensor 302 and determine movement information therefrom. For example, embodiments of processing circuitry 310 operates to analyze (e.g., correlate features within) successive images provided by optical sensor 302. Analysis provided by processing circuitry 310 may operate to determine movement direction, velocity, and/or the like of shaft portion 132 of instrument 130 through instrument guide 112. Processing circuitry 310 may thus provide movement information (e.g., movement along the axis of the insertion angle) to processing circuitry 114 of system unit 110 (FIG. 1A). Such information may be utilized for instrument position determination, image generation, etc.

Communication of information between processing circuitry 310 and processing circuitry 114 may be by wireline (e.g., within or as part of a signal cable connecting imaging transducer 111 and system unit 110) or wireless (e.g., RF or infrared (IR)). Similarly, communication of information between processing circuitry 310 and light source 301 and/or optical sensor 302 may be by wireline or wireless. For example, where opto-mechanical sensor system 113 is provided in a distributed configuration, such as where processing circuitry 310 is disposed within a housing of system unit 110, wireless communication of information controlling light source 301 and information captured by optical sensor 302 may be provided using BLUETOOTH, WIFI (IEEE 802.11), or other wireless protocols (including standardized and proprietary protocols). Alternatively, wireline communication for such information may be provided using USB, $I^2C$ bus, or other wireline protocols (including standardized and proprietary protocols). Where opto-mechanical sensor system 113 is provided in a compact configuration, such as where processing circuitry 310 is disposed in close proximity to light source 301 and optical sensor 302, wireless communication of derived movement information may be provided using BLUETOOTH, WIFI (IEEE 802.11), or other wireless protocols (including standardized and proprietary protocols). Alternatively, wireline communication for such information may be provided using USB, $I^2C$ bus, or other wireline protocols (including standardized and proprietary protocols).

It should be appreciated that, although shown separately in the illustrated embodiment, processing circuitry 310 and 114, or portions thereof, may be combined according to embodiments to provide operation as described herein. For example, processing circuitry 310 may perform one or more of the functions discussed with reference to processing circuitry 114 and/or processing circuitry 114 may perform one or more of the functions discussed with reference to processing circuitry 310.

To accommodate different instrument sizes (e.g., different needle gages), embodiments of mechanical instrument interface 303 comprise a movable or adjustable mount. The illustrated embodiment of mechanical instrument interface 303 comprises movable mount 330 including bias 331 and movable receiver 332. Movable receiver 332 provides support for mechanical instrument interface 303 by a portion of an axel thereof being disposed in movable receiver 332. Bias 331 encourages movable receiver 332 towards instrument support portion 312 of instrument guide 112. Instrument support portion 312 of instrument guide 112 may correspondingly be adapted to accommodate different sizes of instruments. For example, instrument support portion 312 may comprise a "V" groove or other instrument guide. The movable receiver and bias configuration of movable mount 330 allows mechanical instrument interface 303 to move relative to instrument support portion 312 of instrument guide 112 to accommodate instruments of different or differing (e.g., tapered shaft) sizes.

It should be appreciated that mechanical instrument interface 303 of the illustrated embodiment provides a relatively inexpensive, simple configuration. Such an embodiment facilitates a sterile procedure implementation wherein mechanical instrument interface 303 is discarded after use. Although mechanical instrument interface 303 may be discarded, optical sensor system 300 of embodiments may be reused. Thus, although mechanical instrument interface 303 may be disposed within the sterile field of a particular procedure, sterility may be maintained through sterilization of the unit at manufacture and its disposal after use.

To facilitate the reuse of optical sensor system 300, embodiments of the invention provide sterile field separation between mechanical instrument interface 303 and optical sensor system 300. For example, resilient membrane portion 320 of a sterile drape may be disposed between a mechanically separable (e.g., snap together) configuration of mechanical instrument interface 303 and optical sensor system 300. Unlike the embodiment of FIGS. 2A-2C discussed above, the embodiment of FIG. 3 provides a configuration in which appreciable distortion of the sterile drape to accommodate portions of mechanical instrument interface 303 may be foregone. Nevertheless, a sensor energy transparent window (not shown) may be provided to provide a rigid surface for preventing a portion of a sterile drape disposed between optical sensor system 300 and mechanical instrument interface 303 from interfering with the movement of mechanical instrument interface 303. To accommodate the aforementioned transmission of light between light source 301 and optical sensor 302 of optical sensor system 300, such a sensor energy transparent window and the aforementioned portion of the sterile drape are adapted to pass light energy emitted by light source 301.

It should be appreciated that a sensor energy transparent window may be utilized without the aforementioned sterile drape, if desired. For example, a sensor energy transparent window may be utilized to isolate optical sensor system 300 from fluids and other media which may be present in, introduced into, or infiltrate the lumen of instrument guide 112.

Embodiments of opto-mechanical sensor system 113 may omit the aforementioned sensor energy transparent window and/or resilient membrane portion 320 of a sterile drape if desired. For example, the sensor energy transparent window and/or resilient membrane portion 320 may be omitted where opto-mechanical sensor system 113 is disposable, where optical sensor system 300 is adapted to facilitate its sterilization and reuse, etc. Similarly, mechanical instrument interface 303 utilized according to embodiments of the invention may additionally or alternatively be adapted to facilitate its sterilization and reuse.

From the above, it can be appreciated that embodiments of the invention are adapted to provide movement and/or position determinations for non-modified instrument configurations. However, embodiments may provide movement and/or position determinations for instrument configurations which have been modified or otherwise specifically adapted for movement and/or position determinations. Opto-mechanical sensor system 113 may, for example, be used in a configuration of instrument 130 which is adapted for use with a different movement or position determination system. For example, opto-mechanical sensor system 113 of embodiments may ignore such adaptations to the instrument, may use such adaptations (e.g., facets or other perturbations upon a surface of the instrument for facilitating imaging of the instrument) to facilitate communication of movement between shaft portion 132 and interface surface 205, etc.

Regardless of the particular configuration utilized, opto-mechanical sensor system 113 of embodiments comprises commercially available, off-the-shelf optical sensor components. For example, an encoder wheel embodiment of opto-mechanical sensor system 113 (e.g., the embodiment of FIGS. 2A-2C) may comprise a commercially available optical encoder module from the AEDS-964× series of transmissive optical encoder modules available from Avago Technologies Limited. A surface image embodiment of opto-mechanical sensor system 113 (e.g., the embodiment of FIG. 3) may comprise a commercially available ADNS-2610 sensor package available from Avago Technologies Limited. The use of such commercially available components and/or component packages facilitates low cost, highly miniaturized optical sensor systems. The use of such low cost components facilitates disposability of opto-mechanical sensor system 113 (e.g., opto-mechanical sensor system 113, or a portion thereof, may be discarded after use rather than sterilized for reuse). Moreover, opto-mechanical sensor system 113 of embodiments are adapted to provide an unobtrusive addition to various equipment (e.g., instrument guides, ultrasound transducer assemblies, etc.).

In operation according to embodiments of the invention, information regarding movement of instrument 130 provided by opto-mechanical sensor system 113 is utilized in determining movement and/or position of instrument 130, or portions thereof, at block 193 of FIG. 1B. Embodiments utilize information regarding movement of instrument 130 provided by opto-mechanical sensor system 113 in combination with other information to determine a position of instrument 130, or a portion thereof. For example, information regarding the initial position, orientation, insertion angle, etc. of the instrument may be utilized in combination with movement information provided by opto-mechanical sensor system 113 to determine where a portion of interest (e.g., tip 131) of instrument 130 is in relation to a target (e.g., target 102). By knowing the angle of attack or angle of insertion of the instrument relative to an ultrasound transducer (e.g., as defined by instrument guide 112), the relative position of instrument guide 112, and information regarding the movement of instrument 130 trough instrument guide 112, embodiments of the invention operate to calculate the position at any time of any desired portion of the instrument (e.g., tip 131).

Information regarding the angle of insertion provided by instrument guide 112 and the height above the imaging surface of imaging transducer 111 opto-mechanical sensor system 113 is disposed may be provided to processing circuitry 114 for use in determining a position of instrument 130. For example, information regarding the particular instrument guide 112 being used (e.g., the angle of insertion, the position of opto-mechanical sensor system 113, etc.) may be provided automatically using detecting means as shown and described in the above referenced patent application entitled "Medical Device Guide Locator." Additionally or alternatively, such information may be provided manually, such as through user input. Regardless of how such other information is provided to imaging system 100, information regarding movement of instrument 130 as provided by opto-mechanical sensor system 113 is preferably used with such other information to determine a position of instrument 130.

Using information regarding the angle of insertion and the offset of opto-mechanical sensor system 113 above the surface (e.g., the position of opto-mechanical sensor system 113 relative to optical transducer 111), information regarding the movement of instrument 130 through instrument guide 112 may be used to determine a position of tip 131 according to embodiments of the invention. Specifically, as shaft portion 132 of instrument 130 is inserted into a lumen of instrument guide 112, tip 131 passes opto-mechanical sensor system 113, engaging an interface surface of a mechanical instrument interface thereof, whereby an optical sensor system captures information detecting the passing of tip 131 and passes that information to corresponding processing circuitry. Using the information regarding the offset of opto-mechanical sensor system 113, the position of tip 131 relative to target 102 may thus be determined by the processing circuitry. As shaft portion 132 of instrument 130 is inserted further into instrument guide 112, such further motion is detected by opto-mechanical sensor system 113. The processing circuitry (e.g., processing circuitry 210/310 and/or processing circuitry 114) may thus determine movement of shaft portion 132 of instrument 130 through instrument guide 112 and thus determine a present position of tip 131 using the information regarding angle of insertion. Movement determinations for instrument 130 using sensor systems of embodiments of the invention may reliably provide movement detection in relatively small increments (e.g., $3/100$ths of an inch).

The foregoing position information may be utilized in combination with an ultrasound image generated by an ultrasound system unit to display a visual representation of instrument 130, or portion thereof, within an object being imaged (e.g., portion of a patient's internal physiology) at block 194 of FIG. 1B. For example, a marker or icon representing tip 131 of instrument 130 may be superimposed onto an image generated using the imaging transducer. Such a marker may thus be superimposed at a location corresponding to the calculated position of tip 131 within object 101. This operation allows a clinician or other user to visualize the placement of the instrument.

Figure 4:
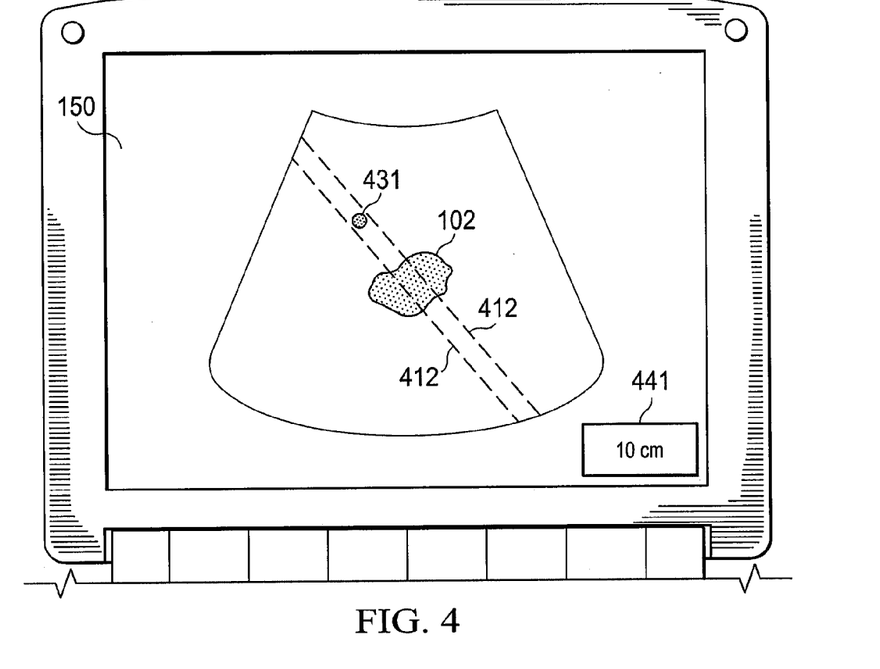
FIG. 4 shows an image generated by the imaging system of FIG. 1A providing information regarding the present position of a portion of an instrument according to an embodiment of the invention.

FIG. 4 shows an embodiment of image 150 generated by imaging system 100 wherein the present position of a portion of instrument 130 is represented visually according to the concepts herein. Image 150 is generated by operation of imaging system 100 to provide a subsurface image of object 101. Thus, image 150 provides an image of target 102 disposed within object 101. Guide lines 412 are provided in the illustrated embodiment to indicate a region in which shaft portion 132 of instrument 130 is expected to pass. For example, using information regarding the position of instrument guide 112 and the angle of insertion provided thereby, guide lines 412 may be determined by processing circuitry 114 and a visual representation thereof generated and superimposed upon the image of object 101. It can be appreciated that a clinician may reference guide lines 412 to move imaging transducer 111 (and correspondingly instrument guide 112 attached thereto) for proper placement to perform a desired procedure (e.g., to position imaging transducer 111 such that shaft portion 132 of instrument 130 will be guided to interface with target 102). As shaft portion 132 of instrument 130 is inserted sufficiently into instrument guide 112, tip 131 will incise a surface of object 101 and proceed into the subsurface. The position of tip 131 will preferably be determined, as discussed above, and when present within the volume of the subsurface being imaged. A marker or other icon may thus be superimposed upon the image of object 101 according to the position determinations of embodiments herein. For example, the illustrated embodiment shows curser 431 representing the present position of tip 131 within object 101. As instrument 130 is inserted further, determinations regarding the present position of tip 131 will be updated and thus curser 431 moved accordingly in operation according to embodiments of the invention.

It should be appreciated that instrument 130 may or may not be visible in the image of object 101. For example, instrument 130 may not be visible due to the relatively small size of shaft portion 132 of instrument 130 inserted into object 101, various obscuring structure present in object 101, the relatively narrow image plane provided by imaging transducer 111, the angle of incidence of imaging signals upon shaft portion 132 of instrument 130, etc. Nevertheless, curser 431 which is updated to represent a present position of instrument 130 within object 101 in real-time without relying upon the imaging technology of imaging transducer 111 (e.g., acoustic imaging) is clearly and readily visible to a clinician or other user of imaging system 100 according to embodiments. Thus, operation as described herein may be utilized to facilitate performance of a desired procedure using instrument 130.

Embodiments of the invention may utilize a marker or icon different than cursor 431 of the illustrated embodiment. For example, embodiments of the invention may utilize one or more instrument pip as shown and described in the above referenced patent application entitled "Systems and Methods for Using Imaging to Assist with Internal Positioning of Instruments." In embodiments using such an instrument pip, a target pip or other graphical target designator may be used in combination with the instrument pip to provide an indication of proper placement of the instrument when the instrument pip is controlled to be disposed in a predetermined position (e.g., concentrically overlapping the target pip).

There is no limitation to the use of instrument markers or icons according to embodiments of the invention. For example, instrument position information may additionally or alternatively be displayed in textual form (e.g., alphanumeric form). Referring again to FIG. 4, the illustrated embodiment of image 150 shows current position information presented in textual form as position depth 441. Position depth 441 shows the depth below a surface of object 101 that tip 131 is currently disposed, as may be determined using movement information and other information as described above. Embodiments may provide additional or alternative textual information, such as position coordinates (e.g., coordinates upon a grid (not shown) of image 150), distance from target (e.g., distance along guide lines 412 between tip 131 and target 102), rate of insertion/extraction (e.g., speed at which instrument is moving within object 101), etc.

Embodiments of an opto-mechanical sensor may be utilized in combination with other techniques for assisting with internal positioning of instruments. For example, opto-mechanical sensor system 113 may be utilized in combination with techniques for enhancing the image of objects within an image. According to embodiments, opto-mechanical sensor system 113 is utilized in combination with enhanced imaging techniques such as those shown in the above reference patent application entitled "Systems and Methods for Enhanced Imaging of Objects Within an Image," to enhance the display of the instrument within a generated image in addition to proving one or more marker, icon, etc. superimposed on the image as described above. Not only may such dual mode embodiments directly provide additional information to a user, but dual mode configurations may be utilized to derive additional data. For example, enhanced imaging techniques may be utilized to detect the actual position of a portion of the instrument within the object. This information may be used to determine that the instrument is not traveling along the predicted path, and thus that a portion thereof (e.g., tip) is not disposed where information such as the insertion angle and distance traveled would suggest. Accordingly, position determinations for one mode may be corrected or modified using information acquired from another mode.

The multiple modalities implemented for providing instrument position information according to embodiments may include modalities which provide similar or dissimilar position determinations. For example, embodiments of the invention implement a mode utilizing techniques which do not rely upon modification of an instrument to determine the position of a portion of the instrument as described herein may also implement a mode utilizing techniques which do rely upon modification of an instrument to determine the position of a portion of the instrument (e.g., as described with reference to some embodiments shown in the above referenced patent application entitled "Systems and Methods for Using Imaging to Assist with Internal Positioning of Instruments").

Warnings and/or other messages may be presented to a user based upon analysis of information from one or more modality. For example, messages may be presented to inform a user that the instrument is traveling along a trajectory outside of an established tolerance, that a mismatch of position information between the modalities beyond a threshold has been detected, etc. Similarly, information regarding the level of confidence regarding a position determination may be provided through analysis of information from multiple modalities.

Although embodiments have been described herein with reference to ultrasound systems providing ultrasound images, it should be appreciated that the concepts of the present invention may be applied to a number of imaging technologies. For example, embodiments of the invention may be utilized with computed tomography (CT) systems, RF (e.g., millimeter wave) scanner systems, fluoroscopy systems, etc.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An imaging system comprising:
    an imaging transducer operable to receive signals for creating an image of an object during performance of a procedure;
    an instrument guide coupled to the imaging transducer, the instrument guide operable to provide guidance for movement of an instrument during performance of the procedure; and
    an opto-mechanical sensor system disposed on the instrument guide, the opto-mechanical sensor system including:
        a rotatable interface surface positioned on an axel having a first diameter;
        a spring that biases the axel of the rotatable interface surface toward the instrument;
        an encoded sensor surface coupled to the rotatable interface surface, wherein the encoded sensor surface has a second diameter that is larger than the first diameter; and
        a light source and optical detector positioned on opposite sides of the encoded sensor surface;
    wherein the rotatable interface surface is arranged to be biased by the spring against an instrument that is positioned between the instrument guide and the rotatable interface surface such that movement of the instrument with respect to the instrument guide rotates the encoded sensor surface between the light source and the optical detector and an arc of rotation of an outer axel of the encoded sensor surface is larger than an arc of rotation of the axel of the interface surface, thereby multiplying the magnitude of the motion of the instrument, and
    wherein the opto-mechanical sensor system is operable to provide instrument movement information regarding movement of the instrument during performance of the procedure.

2. The system of claim 1, wherein the imaging transducer comprises:
    an ultrasound transducer.

3. The system of claim 1, further comprising:
    processing circuitry operable to determine a position of at least a portion of the instrument within the object using information regarding movement provided by the opto-mechanical sensor system; and
    a display operable to display the image created during performance of the procedure, wherein the processing circuitry is further operable to provide an indicator of the determined position of the at least a portion of the instrument for visual depiction on the image.

4. The system of claim 3, wherein the processing circuitry is further operable to analyze instrument position information provided by circuitry other than the optomechanical sensor system in combination with the position determined from movement provided by the opto-mechanical sensor system.

5. A method comprising:
    detecting movement of an instrument using the imaging system of claim 1, the detected movement based on sensor information obtained from the opto-mechanical sensor system of the imaging system and associated with a portion of the instrument external to an object, wherein the instrument has not been specially adapted for movement detection using the opto-mechanical sensor system providing the sensor information; and
    determining a current position of at least a portion of the instrument within the object using the sensor information.

6. The method of claim 5, wherein the detecting movement of the instrument using the imaging system of claim 1 comprises:
    interfacing at least a portion of an interface surface of the mechanical instrument interface of the opto-mechanical sensor system of the imaging system of claim 1 with the instrument; and
    viewing movement of a sensor surface of the mechanical instrument interface of the opto-mechanical sensor system by an optical sensor system of the opto-mechanical sensor system of the imaging system of claim 1.

7. The method of claim 6, wherein the detecting movement of the instrument using the imaging system of claim 1 further comprises:
    providing multiplication of the movement of the instrument by a relationship of the interface surface and the sensor surface for facilitating movement detection by the optical sensor system of the imaging system of claim 1.

8. The method of claim 5, wherein the determining the current position comprises:
    analyzing movement information provided by the detecting movement of the instrument using the imaging system of claim 1 and information regarding a position of the optical sensor to estimate the current position.

9. The method of claim 8, further comprising:
    providing guidance to movement of the instrument during performance of a procedure, wherein the determining the current position further comprises analyzing information regarding the instrument guidance using the imaging system of claim 1 in addition to the movement information and optical sensor position information provided by the imaging system of claim 1.

10. The method of claim 8, further comprising:
    analyzing instrument position information provided by circuitry of the imaging system of claim 1 other than the opto-mechanical sensor system of the imaging system in combination with the current position estimate determined from movement provided by the opto-mechanical sensor system of the imaging system.

11. The method of claim 10, further comprising:
    providing at least one of issuing a message that the instrument is out of position based upon the combined analysis produced by the imaging system of claim 1 and correcting the current position estimate based upon the combined analysis.

12. The method of claim 5, further comprising:
    using the imaging system of claim 1 for displaying an image of at least a portion of the object during performance of the procedure, wherein the image includes an indicator of the current position of the at least a portion of the instrument within the object.

13. The system of claim 1, further comprising a first analyzer configured to process a series of images of the encoded sensor surface provided by the optical detector to determine the movement of the instrument.

14. The system of claim 1, further comprising a sterile field separating the instrument guide and the opto-mechanical sensor system, the sterile field facilitating reuse of the opto-mechanical sensor.

15. The system of claim 14, further comprising a resilient membrane disposed in the sterile field between the instrument guide and the opto-mechanical sensor system, the resilient membrane acting as a barrier to fluids and other media.

16. The system of claim 15, wherein the resilient membrane includes a transparent window used to transmit light between the light source and the optical detector of the opto-mechanical sensor system, thereby enabling operation of the system when the resilient membrane is in use.

* * * * *